United States Patent [19]

Bunte et al.

[11] Patent Number: 5,019,391
[45] Date of Patent: May 28, 1991

[54] SKIN TREATING COMPOSITION, METHOD OF PRODUCING THE SAME AND TREATMENT OF SKIN THEREWITH

[75] Inventors: Thomas Bunte; Wolfgang Parr; Eduard Heyl, all of Berlin, Fed. Rep. of Germany

[73] Assignee: HEYL Chemisch-parmazeutische Fabrik GmbH & Co KG, Fed. Rep. of Germany

[21] Appl. No.: 235,922

[22] Filed: Aug. 23, 1988

Related U.S. Application Data

[63] Continuation-in-part of Ser. No. 209,095, Jun. 17, 1988, abandoned.

[30] Foreign Application Priority Data

Jun. 26, 1987 [DE] Fed. Rep. of Germany ....... 3721190

[51] Int. Cl.$^5$ .............................................. A61K 35/72
[52] U.S. Cl. ................................. 424/195.1; 435/255; 435/256; 435/259; 435/270; 435/942; 530/821; 530/824; 514/8; 514/44
[58] Field of Search ............... 435/259, 270, 942, 255, 435/256; 530/821, 824; 514/8, 44; 424/195.1

[56] References Cited

U.S. PATENT DOCUMENTS

| 3,888,839 | 6/1975 | Newell et al. | 530/824 |
| 4,540,571 | 9/1985 | Schimanski | 424/195.1 |
| 4,767,714 | 8/1988 | Shalitin | 530/824 |

FOREIGN PATENT DOCUMENTS 2222088 11/1974 France ................. 424/94.2

Primary Examiner—Douglas W. Robinson
Assistant Examiner—Jean Witz
Attorney, Agent, or Firm—Steinberg & Raskin

[57] ABSTRACT

A composition for the treatment of the skin comprises a fraction of a mechanically obtained lysate of yeast cultures of the species *Saccharomyces cerevisiae*. The translation system contained in the compositions of the invention are obtained by lysing cultures of *Saccharomyces cerevisiae*. The application of such composition, in any suitable form, such as a cream, ointment, gel or the like, to skin promotes protein biosynthesis by the skin cells so that the metabolism of the extracellular matrix of the skin is restored to the physiologically correct balance and the skin is revitalized.

17 Claims, No Drawings

SKIN TREATING COMPOSITION, METHOD OF PRODUCING THE SAME AND TREATMENT OF SKIN THEREWITH

CROSS REFERENCE TO RELATED APPLICATION

This is a continuation in part of our copending application Ser. No. 209,095 filed Jun. 17, 1988, now abandoned.

BACKGROUND OF THE INVENTION

It is known that the skin in the course of daily work, as well as through natural influences of the environment and the natural aging process, experiences changes. The skin loses its elasticity and flexibility and starts to sag. Seen from the biochemical point of view this is a result of a loss of vitality of the skin cells. These cells are no longer able to synthesize the components of the extracellular matrix in optimum form. Since the majority of the components of the extracellular matrix are proteins, the conclusion can be drawn that the protein-biosynthesis system of the skin cells no longer functions optimally. The consequence is, that on the one hand, sufficient new components of the connective tissue cannot be synthesized and that, on the other hand, not enough proteolytically effective enzymes are produced, which, in turn, could degrade the aged extracellular matrix. Hence, aging of the skin can also be viewed from the standpoint of disturbance of the natural protein turnover. A large number of scientific publications confirms this way of looking at it; see for example:

KANUNGO, M. S., D. KOUL and X. R. REDDY; Concomitant Studies on RNA and Protein Syntheses in Tissues of Rats of Various Ages. Exp. Geront. 5 (1970) 261;

KAO, K. Y. T. and T. H. Mc GAVACK: Connective Tissue XVIII. Age differences in protocollagen hydroxylase of porcine uterine homogenate. Proc. Soc. exper. Biol. (N.Y.) 130 (1969) 491;

KAO, K. T., D. M. HILKER, T. H. Mc GAVACK: Connective Tissue. III. Collagen and hexosamine content of tissues of rats at different ages. Proc. Soc. exp. Biol. 104 (1960) 359;

KAO, K. T., D. M. HILKER and T. H. Mc GAVACK: Connective Tissue, IV. Synthesis and turnover of proteins in tissues of rats. Proc. Soc. exp. Biol. (N.Y.) 106 (1961) 121;

KAO, K. Y. T., D. M. HILKER and T. H. Mc GAVACK: Connective Tissue V. Comparison of synthesis and turnover of collagen and elastin in tissues of rat of several ages. Proc. Soc. Exp. Biol. (N.Y.) 106 (1961).

SUMMARY OF THE INVENTION

It is accordingly a primary object of the present invention to provide cosmetic compositions that act to revitalize the skin and counter the aging processes of the skin.

It is another object of the present invention to provide a method of producing such compositions.

It is yet a further object of the Present invention to provide for the treatment of skin to revitalize the skin in a manner which counters the aging process.

With the above and other objects in view, the present invention mainly comprises as a cosmetic composition for revitalizing of skin, a lysate obtained mechanically from yeast cultures of the species *Saccharomyces cerevisiae*.

The yeast cultures of the species *Saccharomyces cerevisiae* may be lysed in any suitable manner and the translation system obtained by such laming when applied to the skin acts to restore the physiologically correct balance to the skin and revitalizes the same.

The mechanically obtained fractions from the yeast cultures of the species *Saccharomyces cerevisiae* may be applied to the skin topically in any suitable form.

It was surprisingly found that a translation system with the ability to build the proteins of the body can be recovered in a fraction of a lysate, obtained mechanically from the above specified yeast cultures, that promotes protein biosynthesis by the skin cells. The metabolism of the extracellular matrix which, as mentioned, is disrupted by daily tasks, environmental influences and the natural aging process, is restored to the physiologically correct balance, so that the skin is revitalized.

This object is achieved by the cosmetic composition of the present invention that contains a fraction of the lysate obtained mechanically from yeast cultures of the species *Saccharomyces cerevisiae*.

To obtain the translation system contained in the compositions of the invention, cultures of *Saccharomyces cerevisiae* are first lysed. For this purpose cultures of *Saccharomyces cerevisiae*, suitably shaker cultures, are centrifuged, rinsed with physiological saline and centrifuged once again.

The resultant sediment is suspended in a HEPES/KOH buffer of neutral pH which additionally contains magnesium acetate, potassium acetate and sucrose. "HEPES" is chemically known as 4-(2-hydroxyethyl)-1-piperazine ethanosulfonic acid.

The suspension is then lysed at 0° C. by shaking with glass beads 0.05 mm in diameter. A shaking time of 10 minutes is required for complete lysis of 100 ml yeast suspension. Other methods familiar in the literature may also be used to lyse the yeast cells, for example that of T. G. Cooper, Biochemische Arbeitsmethoden, Walter de Gruyter, Berlin New York 1981, pages 338 to 342.

It is helpful if cell nuclei and debris are then removed by centrifuging the lysate.

The fraction employed in the compositions of the invention is preferably the exclusion volume obtained when the lysate is subjected to chromatography (gel filtration) on a molecular sieve. A cross-linked dextran, e.g. Sephadex G-73, is especially suitable for gel filtration.

Particularly preferred for use in the compositions according to the invention is a fraction obtained by further separation of the gel filtration exclusion volume. This separation takes place on a discontinuous gradients (step gradient) preferentially on a sucrose gradient. This gradient usefully consists of the following gradation: 1.8M; 1M; 0.5M, and 0.1M sucrose in 30 mM tris HCl pH 7.5; 200mM KCl; 5 mM $MgCl_2$; 6 mM 2-mercaptoethanol, and 0.25 mM EDTA.

The discontinuous gradient is overlayered with the gel filtration exclusion volume and separation is carried out at 100,000 to 150,000 xg, preferably 130,000 xg. It is helpful to work at cool room temperature (0° to 10° C.; especially 4° C.). The time of separating operation depends on the gradation of the gradient and the magnitude of the centrifugal force, and is generally 10 to 30 hours, advisably 15 to 20 hours. The individual gradations of the gradient will then hold the exclusion volume fractions corresponding to that density. Subfractions can then also be obtained by separating out the individual gradations of the gradient into several layers.

The fractions may be used as such i.e. as solution in standardized form, or, preferably, as lyophilisate. Lyophilization may be effected by any conventional method known in the art.

For use in the compositions of the invention one or more of the fractions that deposited in the individual gradient gradations can be utilized. Also suitable are the heaviest polyribosomes, which do not collect in one of the step gradations, but at the bottom of the centrifuge tube. Especially preferred is the fraction found in the 1.8M gradation of the aforementioned sucrose gradient.

Preferably the fractions used according to the invention do not contain endogenous mRNA. If any is present it can be eliminated by incubating the fraction with Micrococcus nuclease.

The fraction used in the compositions of the invention contain the entire ribosomal protein biosynthesis system, and possibly also tRNA, ATP, GTP and amino acids usual for biosynthesizing protein. These last constituents may also be added if desired. In addition other constituents such as minerals, trace elements, vitamins and other active substances may be added. As mentioned, the fractions of the invention contain ribosomal activity and are capable of reading and translating exogenous mRNA. Their action is assumed to consist of the provision of functioning ribosomal activity which replaces damaged ribosomes. Thus enough ribosomes are again available for translation of amino acids into proteins, promoting the protein biosynthesis of damaged or aging skin.

Suitable fractions according to the invention are those able to read exogenous mRNA and translate it into protein. They are further defined by their sedimentation behaviour in the density gradient and by the way the proteins cooperate in the fraction. These properties are determined as described by B. Schulz-Harder and E. R. Lochmann in Zeitschrift fur Naturforschung 31c (1976), 169-173.

The fractions employed according to the invention are standardized using their ability to incorporate S-35 methionine into protein. This is done as follows:

To 0.5 ml of the fraction there is exogenously added 1 ug m RNA, 2 ml $S^{35}$ - Methionine and the remaining nonradioactive amino acids. The system is then incubated at 30° C. for 30 minutes. Next the three-fold volume (1.5 ml) of 10% trichloroacetic acid is added to precipitate the protein and the system is incubated at 4° C. for 10 minutes. The protein is collected by filtration and dried. The radioactivity present in the precipitated protein is determined in a scintillation counter (see B. Schultz-Harder and E. R. Lochmann, ibid.).

The fractions are adjusted such that in the above standardization method, the fractions give 3000 to 5000 counts/min. in the scintillation counter. The fractions so adjusted are incorporated into the cosmetic compositions as a solution in an amount of 3 to 40%, preferably 5 to 20% by volume or as a lyophilisate in a corresponding amount.

It was shown by means of in vitro and in vivo experiments that the natural rate of protein biosynthesis can be substantially enhanced when the compositions according to the invention are applied. This stimulatory action of the compositions of the invention was proved by the following experiments:

1. In vitro tests on:
a) an ovarian cell line of Chinese hamster;
b) human fibroblasts.

The capacity for biosynthesis of the cells mentioned was blocked completely by the addition of cycloheximide. The cells were then divided into two portions. One portion was incubated along with the fraction being used in accordance with the invention and with the radioactive amino acid S 35 methionine. The other portion was likewise incubated along with S 35 methionine, but this time without the mentioned fraction.

During incubation, protein biosynthesis took place in which the S 35 methionine became incorporated into the proteins. Once the incubation was over the protein were precipitated with acid and the precipitated protein was assayed for the presence of radioactivity.

It was found that the batch treated with the fraction employed in accordance with the invention showed a very significant rate of protein biosynthesis as against the control batch.

2. In vitro tests on mice:

The animals were first injected intracutaneously with cycloheximide on shaved areas of the back to inhibit protein biosynthesis of the skin. Next a cosmetic composition consisting only of the carrier along with S 35 methionine was applied to one group of the mice, and the same cosmetic composition, but this time comprising 15% of the fraction of the invention along with S 35 methionine, was applied to another group of the mice. In each case the quantity of S 35 methioine was 0.1 g.

After an incubation period of 12 hours the mice were killed with ether and the areas of skin were removed. The areas of skin were extracted and then the radioactivity was determined in the proteins which could be precipitated from the extract using acid.

It was found that the composition having the fraction according to the invention enables protein biosynthesis of the skin despite inactivation of the skin protein biosynthesis by cycloheximide. This means that the compositions of the invention are able to enhance protein biosynthesis of the skin cells.

Cosmetic compositions are prepared with the skin treating agents of the present invention for topical application. For this purpose, standard formulations such as creams, ointments, gels, lotions, or compositions for face masks into which they can be worked as a solution or a lyophilisate are used. The amount of the agent used is sufficient to achieve the desired skin revitalizing effect.

These formulations are based on conventional carrier systems such as polyethylene glycols, carboxymethyl cellulose, carboxyvinyl polymerisates, paraffin oil (liquid paraffin), cetylstearyl alcohol, oleic acid ester, fatty acid triglycerides, polyacrylates, glycerol, alcohols and the like. They can also contain conventionally used auxiliary agents such as preservatives, perfume oils, buffers, wetting agents and the like.

DESCRIPTION OF PREFERRED EMBODIMENTS

The following examples are given to further illustrate the invention. The scope of the invention is not, however, meant to be limited to the specific details of the examples. In all examples, percentages are given as percent by volume.

Example 1

Preparation of a w/o cream having the following constituents:

| (a) Cetyl stearyl alcohol | 9.0% |
|---|---|
| Sodium cetyl stearyl sulphate | 1.0% |
| Oleic decyl ester | 10.0% |
| Lanolin | 2.0% |
| Triglyceride from fractionated coconut oil fatty acids | 5.0% |
| Preservative (Phenonip brand of liquid preservatives mixture of p-hydroxybenzoic acid esters and phenoxyethanol) | 0.3% |
| (b) Distilled water | 57.7% |
| 70% solution of sorbitol | 5.0% |
| (c) Protein biosynthesis active substance system: gel filtration exclusion volume (or the corresponding lyophilisate) | 10.0% |

The composition was prepared by first melting ingredient combination a) and heating it to approximately 70° C. and stirring into the resulting melt the solution listed under b). heated to 70° C. Stirring of the whole is continued until the cream has cooled to approximately 35° C. Thereafter component c) is stirred in until it is evenlY distributed.

In piece of the exclusion volume obtained in the gel filtration it is also possible to use one of the fractions obtained when the exclusion volume is separated out on a discontinuous sucrose gradient.

EXAMPLE 2

Prepration of a w/o cream having the following constituents:

| (a) Mixture of high-molecular esters, principally composite esters from pentaerythritol fatty acids ester and citric alcohol ester and mineral fats. | |
|---|---|
| Oleic declyl ester | 20.0% |
| Vegetable oil | 5.0% |
| White Vaseline | 5.0% |
| Preservative (as required) | |
| (b) Distilled water | 55.0% |
| (c) Protein biosynthesis | 15.0% | active substance system: fraction obtained in the 1.8M gradation of the discontinuous sucros gradient (or the corresponding lyophilisate).

The composition was prepared by the method of Example 1.

EXAMPLE 3

Preparation of a gel having the following constituents:

| (a) Water, distilled, preserved | 50.0% |
|---|---|
| Carbopol 40 (polacrylic acid) | 0.5% |
| Phenonip (preservative) | 0.3% |
| (b) Water, distilled, preserved | 28.2% |
| Triethanolamine | 1.0% |
| (c) Protein biosynthesis active substance system: | 20.0% |

Fraction obtained in the 1.8M gradation of the discontinuous sucrose gradient (or the corresponding lyophilisate).

The composition was prepared by a) dispersing the ingredient combination by rapid stirring. Next the solution listed under b) and finally component c) are stirred in.

EXAMPLE 4

Preparation of a lotion having the following constituents:

| (a) Ethanol, 96% by volume | 15.0% |
|---|---|
| (b) Water, distilled, preserved | 76.4% |
| Citric acid | 0.3% |
| Phenonip | 0.3% |
| 1,2 propylene glycol | 3.0% |
| (c) Protein biosynthesis active substance system | 5.0% | c) Protein biosynthesis active substance system 5.0%
Fraction obtained in the 1M and 0.5M gradations of the discontinuous sucrose gradient (or the corresponding lyophilisate)

The composition was prepared by preparing a solution from the ingredients under b). Next component a) is stirred in first, and then component c).

EXAMPLE 5

Preparation of a face mask having the following constituents:

| glycerol monostearate, autoemulgating | 26 g |
|---|---|
| rice starch | 18 g |
| kaolin | 35 g |
| almond bran | 10 g | protein biosynthesis active substance system:
lyophilisate of 30 ml of the gel filtration exclusion volume or of the fraction obtained in the 0.5; 1 or 1.8M gradation of the discontinuous sucrose gradient.

Glycerinmonostearate was pulverized and blended with the other constituents. For use the mixture was stirred with 400 ml hot water to a creamy paste and applied onto the skin at bearable temperature.

The fractions used in examples 1 to 5 were standardized to an amount of protein equivalent to 4000 counts/min. using the above standardization method.

EXAMPLE 6

Shaker cultures of *Saccharomyces cerevisiae* are centrifuged, rinsed with physiological saline, centrifuged again with the sediment re-suspended in a buffer comprising 30mM tris HCl pH 7.5; 200mM KCl; 5mM $MgCl_2$; 500 mM saccharose; 6mM mercaptoethanol; 0.25 mM EDTA; 20% v:v. The re-suspended solution is then lysed at 0° C. by shaking with glass beads 0.05 mm in diameter. 10 minutes shaking is required to lyse 100 ml of the yeast suspension. The homogenate thus obtained is centrifuged for 10 minutes at 18,000 g to remove cell nuclei and cellular debris. The purified supernatant is put onto a Sephadex G 75 molecular sieve column. The exclusion volume is collected and can be used for the compositions of the invention.

The entire exclusion volume is then adjusted to 1% nonionic detergent such as BRij 589 and then overlayed on a discontinuous sucrose gradient. This gradient comprises the following gradations: 1.8M; 1M, 0.5M and 0.1M sucrose in 30 mM tris HCl pH 7.5; 200mM KCl; 5mM $MgCl_2$; 6 mM 2-mercaptoethanol and 0.25 mM EDTA. The batch is centrifuged in a swing-tube rotor at 130 000 xg for 18 hours at 4° C. The gradient is then fractionated. The individual fraction can be used for the compositions of the invention.

If desired, the fractions may be lyophilized by conventional methods.

Application of any of the compositions of the above examples to skin results in a noticeable improvement in the appearance of the skin after a relatively short period of time. The lotion, cream, etc may be applied daily, for example, before going to bed or during any suitable time periods.

While the invention has been described with respect to particular compositions, it is apparent that variations and modifications thereof can be made without departing from the spirit or scope of the invention.

What is claimed is:

1. Cosmetic composition for the treatment of skin, comprising an exclusion volume from gel filtration of a lysate from yeast cultures of the species *Saccharomyces cerevisiae*, wherein
   the isolated fraction promotes protein and biosynthesis of skin cells when applied topically, and
   the active fraction being obtained by
   (a) growing cultures of *Saccharomyces cerevisiae*, centrifuging the same, rinsing with physiological saline and centrifuging to obtain a sediment;
   (b) suspending the thus-obtained sediment in a buffer of neutral pH, and preparing mechanically a lysate of the cells;
   (c) centrifuging the thus-prepared lysate in order to remove cell nuclei and debris;
   (d) subjecting the lysate to gel filtration on a cross-linked dextran to obtain an exclusion volume therefrom; and
   (e) recovering said exclusion volume from the gel filtration.

2. Method of treating skin, which comprises applying to the skin an effective amount of a cosmetic composition for the treatment of skin, comprising an exclusion volume from gel filtration of a lysate from yeast cultures of the species *Saccharomyces cerevisiae*, wherein
   the isolated fraction promotes protein and biosynthesis of skin cells when applied topically, and
   the active fraction is obtained by
   (a) growing cultures of *Saccharomyces cerevisiae*, centrifuging the same, rinsing with physiological saline and centrifuging to obtain a sediment;
   (b) suspending the thus-obtained sediment in a buffer of neutral pH, and preparing mechanically a lysate of the cells;
   (c) centrifuging the thus-prepared lysate in order to remove cell nuclei and debris;
   (d) subjecting the lysate to gel filtration on a cross-linked dextran to obtain an exclusion volume therefrom; and
   (e) recovering said exclusion volume from the gel filtration.

3. Method of producing a composition for cosmetic use, which comprises
   (a) growing cultures of *Saccharomyces cerevisiae*, centrifuging the same, rinsing with physiological saline and centrifuging to obtain a sediment;
   (b) suspending the thus-obtained sediment in a buffer of neutral pH, and preparing mechanically a lysate of the cells;
   (c) centrifuging the thus-prepared lysate in order to remove cell nuclei and debris;
   (d) subjecting the lysate to gel filtration on a cross-linked dextran to obtain an exclusion volume thereof; and
   (e) recovering said exclusion volume from the gel filtration.

4. Method according to claim 3, wherein in step (b), the sediment from the centrifuging is suspended in a buffer of neutral pH containing magnesium acetate, potassium acetate, and sucrose.

5. The composition of claim 1, wherein (b) the lysate is mechanically prepared by shaking with beads.

6. The method of claim 3, wherein (b) the lysate is prepared by shaking with beads.

7. The composition of claim 5, wherein said mercaptoethanol is 2-mercaptoethanol.

8. The composition of claim 5, wherein said gradient is overlayed with said gel filtration exclusion volume and separation is carried out at 100,000 to 150,000 xg., at 0° to 10° C., and over 10 to 30 hours.

9. The composition of claim 8, wherein said separation is carried out at about 130,000 xg., at about 4° C., and over about 15 to 20 hours.

10. The method of claim 13 wherein said gradient is overlayed out at about 130,000 xg., at 0° to 10° C., and over 10 to 30 hours.

11. The method of claim 10, wherein said separation is carried out at about 130,000 xg., at about 4° C., and over about 15 to 20 hours.

12. The composition of claim 1, additionally comprising a carrier selected from polythylene glycols, carboxymethyl cellulose, carbolvinyl polymerisates, paraffin oil or liquid paraffin, cetylstearyl alcohol, oleic acid ester, fatty acid triglycerides, polyacrylates, glycerol, and alcohols.

13. The method of claim 3, wherein said exclusion volume from the gel filtration step is further fractioned on a discontinuous sucrose gradient comprising 1.8M; 1M; 0.5M and 0.1M sucrose in 30 mM tris HCl ph 7.5; 200 mM KCl; 5 mM $MgCl_2$; 6 mM mercaptoethanol and 0.25 mM EDTA.

14. Composition according to claim 15 wherein the fraction is that which comes from the 1.8M gradation of the gradient.

15. Composition according to claim 1 wherein said exclusion volume is fractionated on a discontinuous sucrose gradient comprising 1.8M; 1M; 0.5M and 0.1M sucrose in 30 mM tris HCl pH 7.5; 200 mM KCl; 5 mM $MgCl_2$; 6 mM mercaptoethanol and 0.25 mM EDTA.

16. Composition according to claim 6 wherein said fraction is lyophilized.

17. Composition according to claim 15 wherein said fraction is lyophilized.

18. Composition according to claim 6 wherein said fraction is lyophilized.

* * * * *